United States Patent [19]  [11] 4,076,736
Reubke et al.  [45] Feb. 28, 1978

[54] PREPARATION OF AMINOANTHRAQUINONES FROM NITROANTHRAQUINONES

[75] Inventors: Karl-Julius Reubke, Cologne, Germany; Hans-Samuel Bien, deceased, late of Burscheid, Germany, by Else Bien, nee Geriche, heiress; Gabriele Bien; Dorothee Bien, both of Berscheid, Germany

[73] Assignee: Bayer Aktiengesellschaft, Leverkusen, Germany

[21] Appl. No.: 693,038

[22] Filed: Jun. 4, 1976

[30] Foreign Application Priority Data

Jun. 14, 1975 Germany ............................. 2526651

[51] Int. Cl.² ...................... C07C 87/67; C07C 97/24
[52] U.S. Cl. ................................................. 260/382
[58] Field of Search ......................................... 260/382

[56] References Cited

U.S. PATENT DOCUMENTS

| 3,933,866 | 1/1976 | Seha ..................................... 260/382 |
| 3,933,867 | 1/1976 | Thiem et al. ......................... 260/382 |
| 3,969,374 | 7/1976 | Thiem et al. ......................... 260/382 |

Primary Examiner—Paul F. Shaver
Attorney, Agent, or Firm—Burgess, Dinklage & Sprung

[57] ABSTRACT

In the reaction of a nitroanthraquinone with ammonia in a solvent at elevated temperature to produce the corresponding aminoanthraquinone, the improvement which comprises effecting the reaction in the presence of an ammonium halide. Advantageously, the nitroanthraquinone is an α-nitroanthraquinone, the ammonium halide is at least one of ammonium chloride and ammonium bromide, and the solvent comprises at least one member selected from the group consisting of water, nitrobenzene, a glycol, an acid amide and sulfolane.

10 Claims, No Drawings

PREPARATION OF AMINOANTHRAQUINONES FROM NITROANTHRAQUINONES

The subject of the invention is a process for the preparation of aminoanthraquinones, especially of α-aminoanthraquinones, from the corresponding nitroanthraquinones.

It is known that it is possible to prepare the corresponding aminoanthraquinones from nitroanthraquinones by means of ammonia in water and also in solvents (see Ullmanns Encyklopadie der Technischen Chemie (Ullmann's Encyclopedia of Industrial Chemistry), 4th edition, volume 7, page 591, Weinheim 1973). Usually, impure products which cannot be further processed to dyestuffs without additional purification operations are formed in poor yield acccording to this process. If the reaction of the nitroanthraquinones with ammonia is carried out in water, the effluent is, in addition, deeply colored so that it has to be worked up separately, for example by distillation.

It is also known to carry out the conversion of nitroanthraquinones to aminoanthraquinones with urea or other acid amides (see Ullmann, loc. cit.) and also with ammonium chloride as the sole ammonia donors in certain solvents (see German Offenlegungsschrift (Published Specification) No. 2,211,411). These processes also, which, in addition, are linked to certain solvents, give products which cannot be further processed to dyestuffs without additional purification operations. For example, according to the process of German Ofenlegungsschrift (Published Specification) No. 2,211,411, a distillation of the amino compound is necessary.

All of these processes are also unsuitable for the preparation of α-amino-α'-nitro-anthraquinones from α,α'-dinitro-anthraquinones since product mixtures which are difficult to separate always result.

It is accordingly an object of the present invention to provide a process for the preparation of aminoanthraquinones in good yield, which products are so pure that additional purification operations are not necessary for further processing to give dyestuffs. Furthermore, it is another object of the process according to the invention to provide an advantageous process for the preparation of α-amino-α-nitroanthraquinones.

A process for the preparation of aminoanthraquinones from the corresponding nitroanthraquinones has now been found which is characterized in that nitroanthraquinones are reacted with ammonia in the presence of an ammonium halide and solvents at elevated temperature.

Any desired nitroanthraquinones are suitable as the starting material in the process according to the invention. Preferably, those nitroanthraquinones are employed which contain at least one nitro group in the α-position. For example, nitroanthraquinones of the general formulae I and II

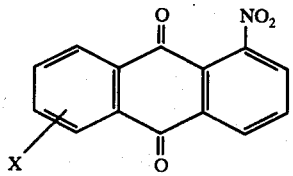 (I)

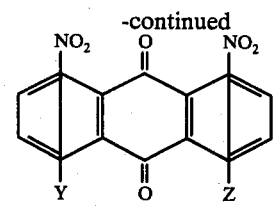 (II)

are suitable for use in the process according to the invention.

The substituent X in the formula I can be H, NO₂, Cl, NH₂, NHR, NHCOR or OR in the 5-, 6-, 7- or 8-position, R denoting any desired, optionally further substituted alkyl, aryl or aralkyl radical with, for example, 1 to 9 C atoms; representative further substituents include chloro, bromo, hydroxy, alkoxy amino, alkylamino, cyano and the like. The substituents Y and Z in formula II can be identical or different and, in each case, OH, OR', NHR'or NHCOR', R' denoting any desired, optionally further substituted alkyl, aryl or aralkyl radical with, for example, 1 to 9 C atoms. The nitro groups in the formula II can be in the 1,5-position or the 1,8-position. 1-Nitroanthraquinone, α,α'-dinitroanthraquinone, α-nitro-α'-acylaminoanthraquinone and α,α'-dinitro-α,α'-dihydroxy are preferentially employed in the process according to the invention.

The process according to the invention is particularly suitable for the selective replacement, in those compounds of the general formulae I and II which carry two nitro groups, at least one of which is in the α-position, of the nitro groups or of an α-nitro group by an amino group and thus for obtaining the corresponding aminonitroanthraquinones. Preferably, α-amino-α'-nitro-anthraquinones which are not further substituted are prepared by the means according to the invention.

The addition of ammonia can be effected in any desired manner. For example, the process according to the invention can be carried out by passing gaseous ammonia under normal pressure or elevated pressure through the reaction mixture. When the process according to the invention is carried out at elevated pressure, it is also possible to use an autoclave in which the desired pressure is set up by appropriate addition of ammonia. Ammonia can also be employed in the form of an aqueous solution. The amount to be added can be varied within wide limits. In general, ammonia is employed in a molar ratio of 2 : 1 to 150 : 1, based on the number of nitro groups to be replaced. Molar ratios of about 5 : 1 to 25 : 1 are preferred.

The process according to the invention is carried out in the presence of an ammonium halide. The hydrohalides of tertiary amines are also possible as the ammonium halide. Suitable ammonium halides are, for example, ammonium chloride, ammonium bromide and ammonium iodide and the hydrochlorides, hydrobromides and hydroiodides of tertiary amines. Suitable tertiary amines, which can be employed in the form of their hydrohalides in the process according to the invention, are, for example: trialkylamines, such as trimethylamine, triethylamine, tri-n-propylamine or dimethyl-n-alkylamines with an alkyl radical with 4 to 20 C atoms, N-alkyl-cyclic-amines, such as N-methylpyrrolidine, N-ethylpyrrolidine, N-methylpiperidine, N-ethylpiperidine or dimethylbenzylamine, or aromatic nitrogen-containing heterocyclic compounds such as pyridine, methylpyridine, dimethylpyridine, trimethylpyridine, quinoline or methylquinoline. It is also possible to use two or more ammonium halides at the same time. Preferably, ammonium chloride or ammonium bromide is used.

The choice of the ammonium halide depends on the reaction medium. The ammonium halide should be completely or partially soluble in the solvent used. The amount of ammonium halide to be employed can be varied within wide limits. In general, it can be between 1 and 200 moles% preferably between about 10 and 150 moles% in each case based on the nitroanthroquinone employed.

The process according to the invention is carried out in the presence of solvents in which the reactants nitroanthraquinone, ammonia and ammonium halide dissolve at least partially under the reaction conditions and which do not themselves react, or do not themselves react to an undesired extent, with one of the reactants. Possible solvents are, in addition to water, organic solvents, such as, for example, aliphatic and cycloaliphatic hydrocarbons, aromatic hydrocarbons, halogenobenzenes and nitrobenzenes, ethers, alcohols, tertiary amines, tertiary amides which are liquid under the reaction conditions, nitriles, sulfones and sulfoxides, as well as any desired mixtures of these solvents.

Suitable aliphatic and cycloaliphatic hydrocarbons are, for example, those with 5 to 12 C atoms, such as n-pentane, n-hexane, n-heptane, cyclohexane, methylcyclohexane, cyclododecane, decalin, cycloheptane, cyclopentane, n-decane, 1,2-dimethylcyclohexane, 1,3-dimethylcyclohexane, 1,4-dimethylcyclohexane, 2,2-dimethylpentane, 2,3-dimethylpentane, 2,4-dimethylpentane, 3,3-dimethylpentane, isopropylhexane, methylcyclohexane, 2-methylheptane, 3-methylheptane, 4-methylheptane, 2-methylhexane, 3-methylhexane, 2-methyloctane, 3-methyloctane, 4-methyloctane, 2-methylpentane, 3-methylpentane, n-octane, pentaisobutane, triethylmethane, 2,2,3-trimethylpentane, 2,2,4-trimethylpentane and 2,3,3-trimethylpentane.

Suitable aromatic hydrocarbons are, for example, those with 6 to 18 C atoms, such as toluene, o-, m- and p-xylene, isopropylbenzene, trimethylbenzene, benzene, diethylbenzene, di-isopropylbenzene, isododecylbenzene, tetralin, naphthalene, methylnaphthalene, diphenyl, diphenylmethane, o-, m- and p-cymene, dibenzyl, dihydronaphthalene, 2,2'-dimethyldiphenyl, 2,3-dimethyldiphenyl, 2,4'-dimethyldiphenyl, 3,3'-dimethyldiphenyl, 1,2-dimethyl-naphthalene, 1,4-dimethyl-naphthalene, 1,6-dimethyl-naphthalene, 1,7-dimethyl-naphthalene, 1,1-diphenylethane, hexamethylbenzene, isoamylbenzene, pentamethylbenzene, 1,2,3,4-tetramethylbenzene, 1,2,3,5-tetramethylbenzene, 1,2,7-trimethylnaphthalene, 1,2,5-trimethylnaphthalene, chlorobenzene, o-dichlorobenzene, trichlorobenzene, chlorotoluene and nitrobenzene.

Suitable ethers are, in particular, aliphatic, cycloaliphatic and aromatic ethers with, for example, 4 to 20 C atoms, such as di-n-butyl ether, di-sec.-butyl ether, di-isopentyl ether, ethylene glycol dimethyl ether, diethylene glycol dimethyl ether, diethylene glycol diethyl ether, methoxycyclohexane, ethoxycyclohexane, dicyclohexyl ether, anisole, phenetole, diphenyl ether, 2-methoxynaphthalene, tetrahydrofuran, dioxane, amyl phenyl ether, benzyl isoamyl ether, dibenzyl ether, diglycol di-n-butyl ether, glycol methylene ether and methyl benzyl ether.

Suitable alcohols are, for example, aliphatic alcohols with 2 to 20 C atoms or glycols with 2 to 5 C atoms, such as ethylene glycol, propylene glycol or their condensation products, such as di-, tri- and poly-ethylene glycols and di-, tri- and poly-propylene glycols, or glycol derivatives, such as ethylene glycol monoalkyl ethers, diethylene glycol monoalkyl ethers and triethylene glycol monoalkyl ethers having alkyl radicals with 1 to 18 C atoms.

Suitable tertiary amines are, for example, trialkylamines, such as, for example, trimethylamine, triethylamine, tri-n-propylamine and dimethyl-n-alkylamine with an alkyl radical with 4 to 20 C atoms, N-alkyl- cyclicamines, such as N-methylpyrrolidine, N-ethylpyrrolidine, N-methylpiperidine and N-ethylpiperidine and dimethylbenzylamine, and aromatic nitrogen-containing heterocyclic compounds, such as, for example, pyridine, methylpyridine, dimethylpyridine and trimethylpyridine, quinoline and methylquinoline.

Suitable teriary amides are; for example, those with 3 to 6 C atoms, such as dimethylformamide, dimethylacetamide, tetramethylurea and N-methylpyrrolidone. Examples of possible sulfones, and sulfoxides are those with 2 to 12 C atoms. Tetramethylenesulfone and dimethylsulfoxide may be mentioned as examples.

Suitable nitriles are, for example, aliphatic nitriles of the formula $C_nH_{2n+1}CN$, in which $n$ can be 1 to 10, and those which carry additional hydroxyl groups, such as, for example, hydroxypropionitrile. Preferably, water, nitrobenzene or solvent mixtures containing nitrobenzene, glycols, acid amides and/or sulfolane are used as solvents. For example, it is possible to use water as the solvent and to carry out the reaction under elevated pressure or to use organic solvents and to carry out the reaction under normal pressure.

The use of mixtures of the indicated solvents is advantageous and, preferably, slightly polar solvents, such as, for example, hydrocarbons, nitrobenzenes or halogenobenzenes, with good dissolving properties for the nitro compound are employed mixed with polar solvents with good dissolving properties for ammonium halides, such as, for example, glycols or tertiary amides.

The process according to the invention is carried out at elevated temperature. The temperature suitable in a particular case depends on the reactivity of the nitro compound, on the solvent and on whether the reaction is carried out under elevated pressure or under normal pressure. The reaction temperature can, for example, be in the range from 80° to 250° C, temperatures ranging from about 100° to 220° C being preferred. When dihydroxy-dinitro-anthraquinones corresponding to the formula II (Y and Z = OH) are employed, the reaction is preferably carried out in the temperature range from 80° to 160° C. When dinitroanthraquinones of the formula I (X = $NO_2$) are employed, the reaction is preferably carried out at temperatures in the range from 140° to 200° C. When nitroanthraquinone corresponding to the formula I (X = H) is employed, the reaction is preferably carried out in the temperature range from 180° to 250° C.

The reaction times can be varied within wide limits and generally depend on the nitro compound employed, the solvent, the temperature and the pressure. The reaction time can be shorter the higher the temperature, the more polar the solvent and the more soluble and the more reactive the nitroanthraquinone employed. In general, the reaction time is 10 minutes to 8 hours, preferably ½ hour to 4 hours.

The process according to the invention can be carried out under normal pressure or under elevated pressure. The pressures can, for example, be between 1 and 100 bars. When dihydroxy-dinitro-anthraquinones corresponding to formula II (Y and Z = OH) or acylamino-nitroanthraquinones corresponding to formula I (X = NHCOR) are converted or when dinitroanthraquinones are converted to aminonitroanthraquinones, the reaction is preferably carried out under normal pressure. When dinitroanthraquinones are converted to diaminoanthraquinones or when 1-nitroanthraquinone is converted to 1-aminoanthraquinone, the reaction is preferably carried out under pressures in the range from 20 to 100 bars.

The process according to the invention can be carried out in customary apparatus, for example in stirred kettles or in stirred autoclaves. A bubble column is also suitable for carrying out the process continuously. In the case of the continuous procedure, the solvent can be recycled directly into the reaction together with excess ammonium halide, after separating off the reaction products, for example by filtration.

Working up of the reaction mixture can be carried out according to processes which are in themselves known, for example by filtering the sparingly soluble reaction products, if appropriate after adding a further solvent, which is miscible with the solvent used for the reaction, in order to render the precipitation complete. For example, when water-soluble solvents, such as glycols, tertiary amides or sulfones, are used, the product can be separated out by precipitation with water or aqueous mineral acids, and filtered off. According to another procedure, the product can be isolated by distilling off part or all of the solvent.

If the nitroanthraquinone employed contains two nitro groups, it is possible to discontinue the reaction after one nitro group has been replaced by the amino group, to work up the reaction mixture and thus to obtain the corresponding amino-nitro-anthraquinone. The time at which the reaction is to be discontinued can be determined, for example, by suitable analytical measures, such as thin layer chromatography or IR spectroscopy.

The advantages of the process according to the invention are that considerably purer products are obtained in better yields than according to the state of the art. The aminoanthraquinones or amino-nitro-anthraquinones prepared according to the invention can be further processed without additional purification operations. When water is used as the solvent, a substantial reduction in the load on the effluent due to organic compounds is achieved, so that direct recycling of the aqueous filtrates is possible. A particular advantage of the process according to the invention is that, under the conditions of this process, α-amino-α'-nitroanthraquinones can be obtained in good yields and high quality. These compounds are indeed in themselves known but hitherto have been accessible only with difficulty.

It was surprising that such good results can be achieved according to the process of the invention since the reactions, mentioned hereinabove, of nitroanthraquinones with ammonia alone or with ammonium chloride alone did not lead to satisfactory products.

The aminoanthraquinones which can be prepared according to the invention are valuable intermediate products for the preparation of dyestuffs (see Ullmanns Encyklopadie der technischen Chemie, (Ullmanns Encyclopedia of Industrial Chemistry), 4th edition, volume 7, page 585 - 646, Weinheim 1973).

EXAMPLE 1A 50 g of 1-nitroanthraquinone (95% pure) in 250 g of tetramethylenesulfone, which contains 3.6% of water, are heated to 180° C, in the presence of 10 g of $NH_4Cl$ and 7.5 liters (STP)/hour of ammonia are passed into this under normal pressure for 5 hours, while stirring vigorously. The mixture is then diluted with 100 g of 18% strength hydrochloric acid and the product is filtered off and washed with water. Yield: 39.5 g of 87.5% pure 1-aminoanthraquinone (= 82.5% of theory).

EXAMPLE 1B (COMPARISON EXAMPLE)

If the same experiment is carried out without the addition of $NH_4Cl$, 33.0 g of 65.0% pure 1-aminoanthraquinone (= 51.2% of theory) are obtained.

EXAMPLE 2A 45 g of 1,5-dinitro-anthraquinone (97% pure) in 400 g of 17.6% strength aqueous ammonia solution, with the addition of 10 g of $NH_4Cl$, are heated to 180° C in a 0.7 l autoclave for 2 hours. After cooling and letting down, the product is filtered off and rinsed with 600 ml of water. This gives 34.5 g of 90.5% pure 1,5-diaminoanthraquinone (89.6% or theory); the product still contains 6.3% (5.5% of theory) of 1-amino-5-nitroanthraquinone. The filtrate is yellow and in a 10 cm cuvette has an extinction of $E_{470}^{10\ cm} = 51$ at λ470 nm.

EXAMPLE 2B (COMPARISON EXAMPLE)

The same experiment without the addition of $NH_4Cl$ gives 34.0 g of 81.5% pure 1,5-diaminoanthraquinone (= 79.5% of theory) containing 6.93% (6.0% of theory) of 1-amino-5-nitroanthraquinone. In this case the effluent is brown and has a $E_{470}^{10\ cm} = 148$.

EXAMPLE 3A 27 liters (STP)/hour of $NH_3$ are passed, under normal pressure, for 2 hours into a suspension of 60 g of 1,5-dinitroanthraquinone (97% pure) and 10 g of $NH_4Cl$ in 500 g of tetramethylenesulfone, at 160° C. After cooling, the mixture is diluted with 1 l of water and the product is filtered off and washed with water. This gives 50.5 g of 1-amino-5-nitroanthraquinone comprising 75.1% (73.0% of theory) of 1-amino-5-nitroanthraquinone and 21.2% (23.2% of theory) of 1,5-diamino-anthraquinone. Total yield: 96.2% of theory.

EXAMPLE 3B (COMPARISON EXAMPLE)

If the same experiment is carried out without the addition of ammonium chloride, 50.5 g of 1-amino-5-nitroanthraquinone comprising 69.0% (67% of theory) of 1-amino-5-nitro-anthraquinone and 20.0% (21.8% of theory) of 1,5-diaminoanthraquinone are obtained. Total yield: 87.0% of theory.

EXAMPLE 4

17.5 liters (STP)/hour of ammonia are passed, under normal pressure, for 40 minutes into a solution of 60 g of 1,5-dinitro-anthraquinone (97% pure) and 5 g of ammonium bromide in 450 g of diethylene glycol, at 220° C, while stirring vigorously. After cooling, the product is filtered off and washed with water. After drying, 46.5 g of 80.5% pure 1-amino-5-nitroanthraquinone (71.5% of theory) are obtained. The product contains 19.0% (19.0% of theory) of 1,5-diaminoanthraquinone.

EXAMPLE 5

25 liters (STP)/hours of ammonia are passed, under normal pressure, at 180° C for 3 hours into a suspension of 60 g of 1,5-dinitro-anthraquinone (97% pure), 114 g of diethylene glycol, 186 g of nitrobenzene and 4.7 g of $NH_4Cl$, at 180° C. After cooling, filtering off the product and washing with methanol, 48.0 g of 86.5% pure 1-amino-5-nitro-anthraquinone (79.3% of theory) containing 11.5% (11.9% of theory) of diaminoanthraquinone and 1.5% of dinitroanthraquinone are obtained.

EXAMPLE 6

Ammonia is passed under normal pressure, at a rate of flow of 20 liters (STP)/hour for 1 hour into a solution of 60 g of 1,8-dinitro-anthraquinone (98.5% pure) and 5 g of $NH_4Br$ in 250 g of diethylene glycol, at 200° C. After working up as in Example 4, 47.0 g of 90.5% pure 1-amino-8-nitro-anthraquinone (80.5% of theory) containing 5.1% of 1,8-diamino-anthraquinone are obtained.

EXAMPLE 7

20 g of 1,8-dihydroxy-4,5-dinitro-anthraquinone in 80 g of nitrobenzene and 20 g of diethylene glycol are reacted in the presence of 2 g of $NH_4Br$ at 150° C for 4 hours with ammonia under normal pressure by bubbling a stream of 17 liters (STP)/hour $NH_3$ into the mixture. After cooling, the product is filtered off and washed with methanol. This gives 16.9 g of approximately 85% pure 1,8-dihydroxy-4-amino-5-nitro-anthraquinone.

EXAMPLE 8

20 liters (STP)/hours of ammonia are passed, under normal pressure, for 40 minutes into a solution of 60 g of a mixture consisting of 1,6-, 1,7- and 1,8-dinitroanthraquinone (41% of 1,6-dinitroanthraquinone, 39% of 1,7-dinitroanthraquinone and 17% of 1,8-dinitroanthraquinone) and 5 g of $NH_4Br$ in 200 g of diethylene glycol, at 180° C. After cooling, filtering off the product and washing with water, 48.5 g of 1-amino-(6,7)-nitroanthraquinone, 38.2% of 1-amino-7-nitroanthraquinone and 44.1% of 1-amino-6-nitro-anthraquinone (92% of theory) are obtained.

EXAMPLE 9

74.4 g of 1-benzoylamino-5-nitro-anthraquinone (94% pure) in 220 g of diethylene glycol with 5 g of $NH_4Br$ are reacted at 200° C for 2½ hours with 22 liters (STP)/hours of ammonia under normal pressure. After cooling, the product is worked up as in Example 4. Yield: 63.0 g of 90.1% pure 1-benzoylamino-5-aminoanthraquinone (88.3% of theory) containing 0.3% of 1,5-dibenzoylamino-anthraquinone, 0.7% of 1,5-diaminoanthraquinone, 1.7% of 1,8-diaminoanthraquinone and 0.7% of 1-benzoylamino-8-amino-anthraquinone.

EXAMPLE 10

29 g of 1-chloro-5-nitro-anthraquinone in 115 g of tetramethylenesulfone are reacted in the presence of 5 g of $NH_4Br$ with 22 liters (STP)/hour of $NH_3$ for 90 minutes at 160° C under normal pressure. The starting material can no longer be detected in a thin layer chromatogram. After diluting with water, the product is filtered off and washed. Yield: 25.0 g of 1-chloro-5-aminoanthraquinone (Cl: 13.0, calculated 12.9%). If the reaction is carried out in the presence of xylene in a water separator, the reaction can be followed by monitoring the amount of water separated.

EXAMPLE 11

45 g of 1,5-dinitroanthraquinone (97 %) are heated to 200° C in 100 ml of water in a 0.7 liter steel autoclave. 300 ml of a cold, 25% strength aqueous ammonia solution, which contains 10% of $NH_4Cl$, are pumped into this mixture over a period of 30 minutes. Thereafter, the temperature is kept constant for another 5 ½ hours, the pressure thereby rising to 60 bar. The product is left to cool without outside help, the pressure released and the product filtered off with suction. The entire filtrate, 350 ml, is faintly yellow in color, $E_{470}^{10\,cm} = 6.0$. After washing and drying there are obtained 34.8 g of 93.0 % pure 1,5-diaminoanthraquinone (92.7 % of theory). The product still contains 4.5 % (4.0 % of theory) of 1-amino-5-nitroanthraquinone.

EXAMPLE 12 A 75 g of 1-nitroanthraquinone (98.5 % strength) are heated to 180° C in 145 ml of water. Thereafter, a cold solution of 14.6 g of $NH_4Cl$ in 240 ml of 25 % strength aqueous ammonia is pumped into this mixture within 5 minutes. The temperature is kept constant for 1 hour, the pressure rising during this period to 51 bar. After cooling and releasing pressure, the product is filtered off by suction and washed with water. Both filtrate and washing water (1 liter) are slightly yellow in color, $E_{470}^{10\,cm} = 13.0$. 66.7 g of 95.2 % pure 1-aminoanthraquinone (97.5 % of theory) are obtained. The product still contains about 1.0% of 1-nitroanthraquinone.

EXAMPLE 12 B (COMPARISON EXAMPLE)

If the experiment is repeated using $NH_3$ solution without the $NH_4Cl$ additive, then the pressure only rises to 35 bar, the effluent has a deeper color ($E_{470}^{10\,cm} = 52.0$), the yield: 65.2 g of 94.1 % pure 1-amino-anthraquinone (94.2 % of theory).

It will be appreciated that the instant specification and examples are set forth by way of illustration and not limitation, and that various modifications and changes may be made without departing from the spirit and scope of the present invention.

What is claimed is:

1. In the reaction of a nitroanthraquinone with ammonia in a solvent at elevated temperature to produce the corresponding aminoanthraquinone, the improvement which comprises effecting the reaction in the presence of an ammonium halide.

2. A process according to claim 1, wherein the nitroanthraquinone is an α-nitroanthraquinone.

3. A process according to claim 1, wherein the nitroanthraquinone is a dinitroanthraquinone and the reaction is discontinued after one nitro group has been replaced by the amino group.

4. A process according to claim 1, wherein the ammonium halide is at least one of ammonium chloride and ammonium bromide.

5. A process according to claim 1, wherein the solvent comprises at least one member selected from the group consisting of water, nitrobenzene, a glycol, an acid amide and sulfolane.

6. A process according to claim 1, wherein the solvent is water and the reaction is effected under elevated pressure.

7. A process according to claim 1, wherein the solvent is an organic solvent and the reaction is effected at normal pressure.

8. A process according to claim 1, wherein the reaction is effected at a temperature from about 80° to 250° C.

9. A process according to claim 8, wherein the nitroanthraquinone is an α-nitroanthraquinone, the ammonium halide is at least one of ammonium chloride and ammonium bromide, and the solvent comprises at least one member selected from the group consisting of water, nitrobenzene, a glycol, an acid amide and sulfolane.

10. A process according to claim 3 wherein the dinitroanthraquinone is an α,α'-dinitroanthraquinone.

* * * * *